US006974581B1

(12) United States Patent
Loosmore et al.

(10) Patent No.: US 6,974,581 B1
(45) Date of Patent: *Dec. 13, 2005

(54) **MULTI-COMPONENT VACCINE COMPRISING AT LEAST TWO ANTIGENS FROM *HAEMOPHILUS INFLUENZAE* TO PROTECT AGAINST DISEASE**

(75) Inventors: Sheena M. Loosmore, Aurora (CA); Yan-Ping Yang, Willowdale (CA); Michel H. Klein, Willowdale (CA)

(73) Assignee: Aventis Pasteur Limited, Toronto (CA)

( * ) Notice: Subject to any disclaimer, the term of this patent is extended or adjusted under 35 U.S.C. 154(b) by 0 days.

This patent is subject to a terminal disclaimer.

(21) Appl. No.: 09/210,995

(22) Filed: Dec. 15, 1998

(51) Int. Cl.[7] .................. A61K 39/102; A61K 39/00; A61K 39/38; A61K 39/385; A61K 39/02

(52) U.S. Cl. ..................... 424/256.1; 424/184.1; 424/193.1; 424/203.1; 424/234.1; 435/69.1; 435/69.3

(58) Field of Search ................... 424/93.2, 200.1, 424/201.1, 202.1, 256.1, 282.1, 163.1, 184.1, 424/193.1, 203.1, 234.1; 435/6, 7.32, 69.1, 435/252.3, 69.3; 514/44; 530/350

(56) References Cited

U.S. PATENT DOCUMENTS

| 5,506,139 A | * | 4/1996 | Loosmore et al. | ........ 435/252.3 |
| 5,549,897 A | * | 8/1996 | Barenkamp et al. | ........ 424/256 |
| 5,750,116 A | * | 5/1998 | Brinton, Jr. | ............ 424/242.1 |

FOREIGN PATENT DOCUMENTS

| EP | 0 208 375 | * | 2/1986 | ......... A61K 39/116 |
| EP | WO 93/24148 | * | 12/1993 | ......... A61K 39/295 |
| US | 0320942 | * | 12/1987 | ......... C07H 15/04 |
| WO | WO 96/37222 | * | 11/1996 | ......... A16K 39/385 |
| WO | WO 97/36914 | * | 10/1997 | ......... C07H 221/02 |

OTHER PUBLICATIONS

Barenkamp et al. 1996. Identification of a second family of high-molecular-weight adhesion proteins expressed by nontypable Haemophilus influenzae. Molecular Microbiology. 19(6): 1215-1223.*

Barenkamp . 1996. immunization with High-Molecular-Weight Adhesion Proteins of Nontypeable Haemophilus influenzae Modifies Experimental Otitis Media in Chinchillas. Inflection and Immunity. 64(4): 1246-1251, 1996.*

* cited by examiner

*Primary Examiner*—Lynette R. F. Smih
*Assistant Examiner*—Ja-Na Hines

(57) ABSTRACT

A multi-component immunogenic composition confers protection on an immunized host against infection caused by *Haemophilus influenzae*. Such composition comprises at least two different antigens of *Haemophilus influenzae*, one of which is an adhesin. High molecular weight (HMW) proteins of non-typeable *Haemophilus influenzae* enhance the immune response in a host to a non-proteolytic analog of Hin47 protein in such immunogenic compositions with one component not impairing the immunogenicity of the other. The *Haemophilus* vaccine may be combined with DTP component vaccines to provide a multi-valent component vaccine without impairment of the immunogenic properties of the other antigens.

19 Claims, 14 Drawing Sheets

Groups of 5 mice were immunized with 0.3 ug of H91AHin47 on day 1 in the presence of various amounts of rHMW. Blood samples were collected on days 14 and 28.

*Statistical significance was found when compared to the control group by student *t* test Groups of 5 mice were immunized with 10 ug of rHMW on day 1 in the presence of various amounts of H91AHin47. Blood samples were collected on days 14 and 28.

*Statistical significance was found when compared to the control group by student *t* test

**Protective Ability of A Two-component *H. influenzae* Vaccine Against NP Colonization with NTHi Strain 12 in Chinchillas**

1. H91AHin47 + rHMW
2. H91AHin47
3. rHMW
s. Supernatant of alum suspension
p. Aluminium sulfate adsorbed proteins

MULTI-COMPONENT VACCINE COMPRISING AT LEAST TWO ANTIGENS FROM *HAEMOPHILUS INFLUENZAE* TO PROTECT AGAINST DISEASE

FIELD OF INVENTION

The present invention relates to the field of vaccinology and, in particular, to the multi-component vaccine comprising recombinant *Haemophilus influenzae* proteins which is useful in protecting against disease caused by *Haemophilus influenzae*, including otitis media.

BACKGROUND OF THE INVENTION

*Haemophilus influenzae* is the cause of several serious human diseases, such as meningitis, epiglottitis, septicemia and otitis media. There are six serotypes of *H. influenzae*, designated a to f, that are identified by their capsular polysaccharide. *H. influenzae* type b (Hib) was a major cause of bacterial meningitis until the introduction of several Hib conjugate vaccines in the 1980's (ref. 1. Throughout this application, various references are referred to in parenthesis to more fully describe the state of the art to which this invention pertains. Full bibliographic information for each citation is found at the end of the specification, immediately preceding the claims. The disclosures of these references are hereby incorporated by reference into the present disclosure). Vaccines based upon *H. influenzae* type b capsular polysaccharide conjugated to diphtheria toxoid (ref. 2), tetanus toxoid (ref. 3 and U.S. Pat. No. 4,496,538), or *Neisseria meningitidis* outer membrane protein (ref. 4) have been effective in reducing *H. influenzae* type b-induced meningitis. The other serotypes of *H. influenzae* are associated with invasive disease at low frequencies, although there appears to be an increase in the incidence of disease caused by these strains as the incidence of Hib disease declines (refs. 5, 6). Non-encapsulated or non-typeable *H. influenzae* (NTHi) are also responsible for a wide range of human diseases including otitis media, epiglottitis, pneumonia and tracheobronchitis. The incidence of NTHi-induced disease has not been affected by the introduction of the Hib vaccines (ref. 7).

Otitis media is the most common illness of early childhood, with 60 to 70% of all children, of less than 2 years of age, experiencing between one and three ear infections (ref. 8). Chronic otitis media is responsible for hearing, speech and cognitive impairments in children. *H. influenzae* infections account for about 30% of the cases of acute otitis media and about 60% of chronic otitis media. In the United States alone, treatment of otitis media costs between 1 and 2 billion dollars per year for antibiotics and surgical procedures, such as tonsillectomies, adenoidectomies and insertion of tympanostomy tubes. It is estimated that an additional $30 billion is spent per annum on adjunct therapies, such as speech therapy and special education classes. Furthermore, many of the causative organisms of otitis media are becoming resistant to antibiotic treatment. An effective prophylactic vaccine against otitis media is thus desirable.

During natural infection by NTHi, surface-exposed outer membrane proteins that stimulate an antibody response are potentially important targets for bactericidal and/or protective antibodies and therefore potential vaccine candidates. Barenkamp and Bodor (ref. 9) demonstrated that convalescent sera from children suffering from otitis media due to NTHi, contained antibodies to high molecular weight (HMW) proteins. About 70 to 75% of NTHi strains express the HMW proteins and most of these strains contain two gene clusters termed hmw1ABC and hmw2ABC (refs. 10, 11). The HMWA proteins have been demonstrated to be adhesins mediating attachment to human epithelial cells (ref. 12). Immunization with a mixture of native HMW1A and HMW2A proteins resulted in partial protection in the chinchilla intrabulla challenge model of otitis media (ref. 13).

U.S. Pat. No. 5,603,938 (Barenkamp), assigned to St. Louis University and Washington University and the disclosure of which is incorporated herein by reference, describes the cloning, expression and sequencing of the genes encoding the HMW1 and HMW2 proteins from strain 12 of non-typeable *Haemophilus*. The HMW proteins are a family of proteins from non-typeable *Haemophilus* of molecular weight of about 120 to 125 kDa which are found in non-typeable *Haemophilus* strains. The HMW proteins are absent from encapsulated strains of *Haemophilus*.

The production of native HMW proteins from *H. influenzae* strains is very low and a method for producing protective recombinant HMW (rHMW) proteins has been described in copending U.S. patent application Ser. No. 09/167,568 filed Oct. 7, 1998, assigned to the assignee hereof and the disclosure of which is incorporated herein by reference. A chinchilla nasopharyngeal colonization model has been developed specifically to demonstrate vaccine efficacy of adhesins (ref. 14) and the rHMW proteins are protective in this model as described in the aforementioned copending U.S. patent application Ser. No. 09/167,568. The rHMW1A and rHMW2A proteins were shown to afford equivalent protection to each other and the rHMW1A protein was chosen for further vaccine studies. In this application, rHMW refers to the recombinant HMW1A proteins from NTHi strain 12, although the corresponding recombinant HMW1A protein from other NTHi strains and the corresponding rHMW2A protein from NTHi strains may be employed for the rHMW. The corresponding naturally-occurring proteins may be employed.

When under environmental stress, such as high temperature, organisms overproduce stress response or heat shock proteins (hsps). Bacterial hsps have been shown to be important immunogens, stimulating both B cells and T cells (ref. 16). The bacterial HtrA or DegP heat shock proteins are expressed under conditions of stress and the *H. influenzae* HtrA protein has been shown to be a partially protective antigen in the intrabulla challenge model of otitis media (ref. 17). The HtrA proteins are serine proteases and their proteolytic activity makes them unstable. In addition, as components of a multicomponent vaccine, the wild-type HtrA protein will degrade admixed antigens. The site-directed mutagenesis of the *H. influenzae* htrA gene (termed hin47) and the properties of the mutants have been fully described in U.S. Pat. No. 5,506,139 (Loosmore et al), assigned to the Assignee hereof and the disclosure of which is incorporated herein by reference. The non-proteolytic HtrA analogue, H91A Hin47, has been shown to be a protective antigen against bacteremia caused by *H. influenzae* type b and against otitis media caused by non-typeable *H. influenzae* (ref. 17). Such analog is used herein, although any other non-proteolytic analog of Hin47 may be employed. HtrA was found in all strains examined, including all encapsulated strains of *H. influenzae*.

Although the main goal of a prophylactic vaccine against *H. influenzae* disease, including otitis media, is to prevent the establishment of nasopharyngeal colonization by including an adhesin as immunogen, the HMW proteins are not present in encapsulated *H. influenzae* or in about 25% of NTHi strains. Therefore, a combination vaccine comprised of at least one adhesin molecule and an additional protective antigen found in all *H. influenzae* strains, will provide better coverage against disease and a broad spectrum of disease protection.

It would be desirable to provide efficacious combination vaccines comprising *H. influenzae* components containing selected relative amounts of selected antigens.

SUMMARY OF THE INVENTION

The present invention is directed towards the provision of a multi-component vaccine to protect against disease caused by infection with *Haemophilus influenzae*, including otitis media.

In accordance with one aspect of the present invention, there is provided an immunogenic composition for conferring protection in a host against disease caused by infection by *Haemophilus influenzae*, including otitis media, comprising at least two different antigens of *Haemophilus influenzae*, at least one of which antigens is an adhesin.

The antigen which is an adhesin may be a high molecular weight protein (HMW) of a non-typeable strain of *Haemophilus*, particularly an HMW1 or HMW2 protein of the non-typeable strain, which may be produced recombinantly.

The antigen of *Haemophilus influenzae* which is not an adhesin may be a non-proteolytic heat shock protein of a strain of *Haemophilus influenzae*. The non-proteolytic heat shock protein of a strain of *Haemophilus influenzae* may be an analog of *Haemophilus influenzae* Hin47 protein having a decreased protease activity which is less than about 10% of that of the natural Hin47 protein.

In accordance with a preferred embodiment of this aspect of the invention, there is provided an immunogenic composition for conferring protection in a host against disease caused by *Haemophilus influenzae*, including otitis media, which comprises:

an analog of *Haemophilus influenzae* Hin47 protein having a decreased protease activity which is less than about 10% of that of natural Hin47 protein, and a high molecular weight (HMW) protein of a strain of non-typeable *Haemophilus influenzae*.

In such composition, the HMW protein may be present in an amount which enhances the immune response in the host to the Hin47 protein analog while there is no interference between the components with respect to their individual immunogenicities.

The analog of Hin47 protein may be one in which at least one amino acid of the natural Hin47 protein contributing to protease activity has been deleted or replaced by a different amino acid and which has substantially the same immunogenic properties as natural Hin47 protein.

Such at least one amino acid may be selected from the group consisting of amino acids 91, 121 and 195 to 207 of natural Hin47 protein. Specific mutants which may be used including serine-197 replaced by alanine, Histidine-91 replaced by alanine, lysine or arginine and Asp-121 replaced by alanine.

The HMW protein of the non-typeable strain of *Haemophilus influenzae* may be a HMW1 or HMW2 protein and may be recombinantly produced. The HMW1 and HMW2 proteins are derived from the respective strains of non-typeable *Haemophilus influenzae* and possess respective molecular weights as set forth in the following Table I:

TABLE I

| Molecular Weight (kDa) | Non-typeable *H. influenzae* Strain | | | | | |
|---|---|---|---|---|---|---|
| | 12 | JoyC | K21 | LCDC2 | PMH1 | 15 |
| Mature Protein: | | | | | | |
| HMW1 | 125 | 125.9 | 104.4 | 114.0 | 102.4 | 103.5 |
| HMW2 | 120 | 100.9 | | 111.7 | 103.9 | 121.9 |

The immunogenic composition of the invention may be further formulated with an adjuvant. Such adjuvant for use in the present invention may include (but not limited to) aluminum phosphate, aluminum hydroxide, QS21, Quil A, derivatives and components thereof, ISCOM matrix, calcium phosphate, calcium hydroxide, zinc hydroxide, a glycolipid analog, an octadecyl ester of an amino acid, a muramyl dipeptide, polyphosphazene, ISCOPREP, DC-chol, DDBA and a lipoprotein and other adjuvants. Advantageous combinations of adjuvants are described in copending U.S. patent applications Ser. No. 08/261,194 filed Jun. 16, 1994 and Ser. No. 08/483,856 filed Jun. 7, 1995, assigned to the assignee hereof and the disclosures of which are incorporated herein by reference (WO 95/34308, published Nov. 21, 1995). The adjuvant preferably may comprise aluminum phosphate or aluminum hydroxide (collectively known as alum).

The components of the immunogenic composition may be present in appropriate quantities to provide the desired immune response. The components may be formulated as a vaccine for in vivo administration to the host. The vaccine composition may contain about 25 to about 100 μg of the Hin47 protein and about 25 to about 100 μg of the HMW protein.

The immunogenic compositions may be formulated with other antigenic components to provide a multivalent vaccine in which the additional antigenic component(s) confer protection against disease caused by another pathogen(s). Such additional antigens should be such that and be present in quantities that the immunogenicity of the individual components of the resulting vaccine is not impaired by other individual components of the composition. Such additional antigens preferably are purified antigens in defined quantities to produce a component vaccine.

Such additional antigens may be those traditionally found in multivalent protective vaccines, such as diphtheria toxoid, tetanus toxoid and pertussis antigens, including pertussis toxoid, filamentous hemagglutinin, pertactin and/or agglutinogens.

The resulting multivalent vaccine also may contain non-virulent poliovirus, such as inactivated poliovirus, which may be type 1, type 2 and/or type 3 poliovirus. The multi-component vaccine further may comprise a conjugate of a tetanus or diphtheria toxoid and a capsular polysaccharide of *Haemophilus influenzae*, preferably PRP-T.

The invention extends to a method of immunizing a host against disease caused by infection by *Haemophilus influenzae*, including otitis media, which comprises administering to the host an immunoeffective amount of the immunogenic composition provided herein.

Advantages of the present invention include a multi-component vaccine that can confer protection against encapsulated and non-encapsulated *Haemophilus influenzae* diseases in a safe and efficacious manner.

BRIEF DESCRIPTION OF DRAWINGS

The present invention will be further understood from the following description with reference to the drawings, in which.

GENERAL DESCRIPTION OF THE INVENTION

Figure 1:
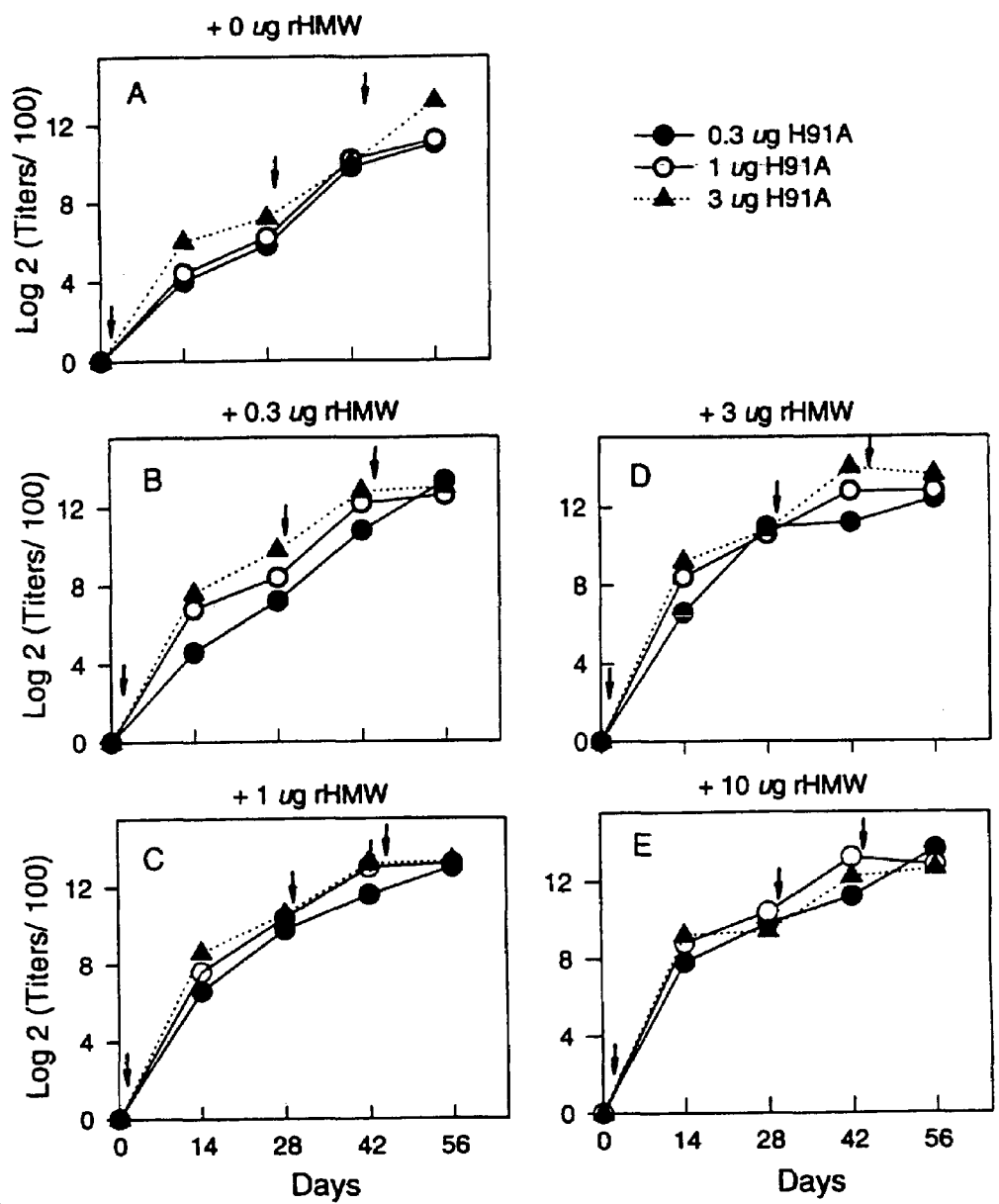
FIG. 1, having Panels A to E, shows the anti-H 91A Hin47 immune responses for H91A Hin47+rHMW combination vaccines in mice. Panel A, no added rHMW; panel B, 0.3 μg of rHMW added; panel C, 1.0 μg of rHMW added; panel D, 3.0 μg of rHMW added; panel E, 10 μg of rHMW added. The arrows indicate the timing of the immunizations.

Colonization of the nasopharynx is the first step in disease development for many bacterial or viral pathogens, including *Haemophilus influenzae*, and vaccines containing adhesin molecules should protect against this first step in disease progression. The high molecular weight (HMW) proteins, found in approximately 75% of non-typeable *H. influenzae*, have been shown to be adhesins that are protective against colonization when administered in a vaccine composition. The HMW proteins are not present in encapsulated *H. influenzae* strains or in about 25% of non-typeable *H. influenzae* strains, and hence they are not sufficient alone, for a vaccine having strain-wide protectivity.

The HtrA protein or Hin47 is found in all encapsulated and non-typeable *H. influenzae* strains. Hin47 is protective against bacteremia caused by *H. influenzae* type b and otitis media caused by non-typeable *H. influenzae*, but it does not itself prevent colonization. Hin47 is proteolytic and cannot itself be used in protein formulations. A combination vaccine comprising HMW and non-proteolytic Hin47 antigens may be formulated to protect against significant *H. influenzae* disease, including otitis media. The present invention provides such combination vaccine.

U.S. Pat. No. 5,506,139 (Loosmore et al) describes the preparation of analogs of *Haemophilus influenzae* Hin47 protein which have a decreased protease activity which is less than about 10% of that of the natural Hin47 protein and which preferably have substantially the same immunogenic properties as natural Hin47 protein. The patent also describes the isolation, purification and characterization of nucleic acid molecules encoding the Hin47 analogs. The natural Hin47 protein is immunologically conserved among non-typeable and type b isolates of *H. influenzae*. The amino acid sequence of the natural Hin47 protein and the nucleotide sequence of the encoding hin47 gene are described in WO 94/00149 published Jan. 6, 1994 and incorporated herein by reference.

The Hin47 analogs of U.S. Pat. No. 5,506,139 are prepared by deleting or replacing by a different amino acid at least one amino acid of the natural Hin47 contributing to protease activity or by inserting at least one amino acid into the natural Hin47 protein, as specifically described therein. The at least one deleted or replaced amino acid may be selected from amino acids 195 to 201 of Hin47 and specifically may be Serine-197, which may be deleted or replaced by alanine. In addition, the at least one deleted or replaced amino acid may be His-91 and may be deleted or replaced by alanine, lysine or arginine. Furthermore the at least one deleted or replaced amino acid may be Asp-121 and may be deleted or replaced by alanine.

In copending U.S. patent application Ser. No. 08/487,167 filed Jun. 7, 1995, assigned to the assignee hereof and the disclosure of which is incorporated herein by reference, there are described multiple mutations effected at different amino acids of the natural Hin47 protein to provide the non-proteolytic Hin47 analog.

In the present invention, the mutation of histidine 91 to alanine (sometimes termed herein "H91A") is employed as illustration of the mutant Hin47 protein, although other Hin47 mutants with reduced protease activity as described in the aforementioned patent and application may be used.

The preparation of the HMW protein recombinantly (rHMW) is described in the aforementioned copending U.S. patent application Ser. No. 09/167,568.

The composition of multi-component vaccines is critical. The vaccine components must be compatible and they must be combined in appropriate ratios to avoid antigenic interference and optimize any possible synergies. If administered with other established vaccines, they must not interfere with the protection afforded by the vaccine against other disease (s).

In specific experimentation performed herein, various antigen ratios were compared for a two component H91A Hin47+rHMW vaccine, in two animal species. Antigenic interference was observed for increasing amounts of H91A Hin47 when combined with a low dose of rHMW, however, this effect disappeared at higher doses of rHMW. There was a synergistic effect observed for increasing amounts of rHMW on the primary antibody response to a low dose of H91A Hin47 and H91A Hin47 improved the primary response to rHMW, if the rHMW were not present in low doses. These findings are surprising in that a single antigen (H91A Hin47) can have both a suppressive and an enhancing effect on another antigen (rHMW) depending on the dose of rHMW present. It was also surprising that rHMW would enhance the vigorous antibody response to H91A Hin47, since it is a weaker immunogen.

Figure 11B:
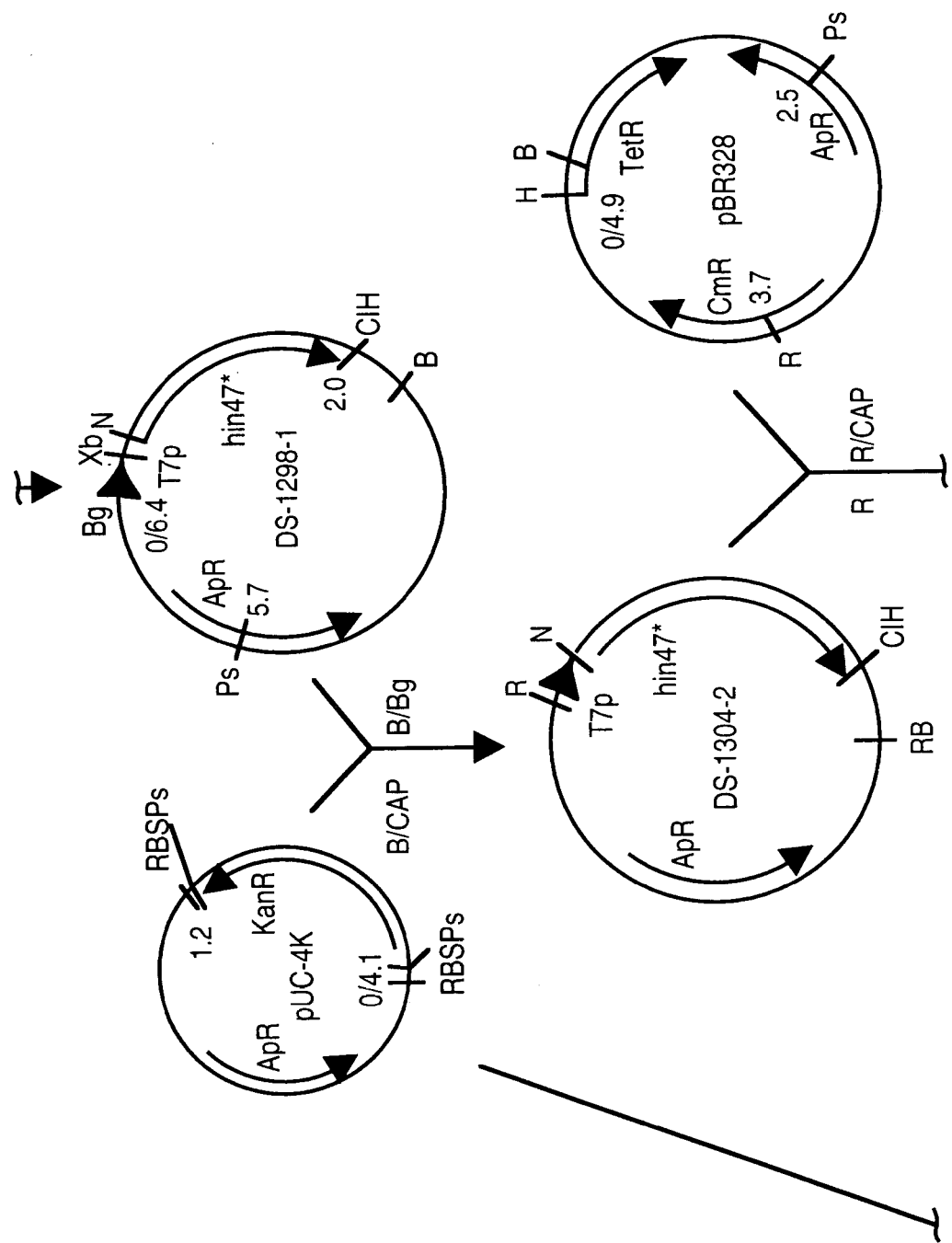
FIG. 11 shows a construction scheme for the preparation of plasmid DS-2150-1 containing the mutant H91A hin47 gene under control of a T7 promoter.
Figure 11C:
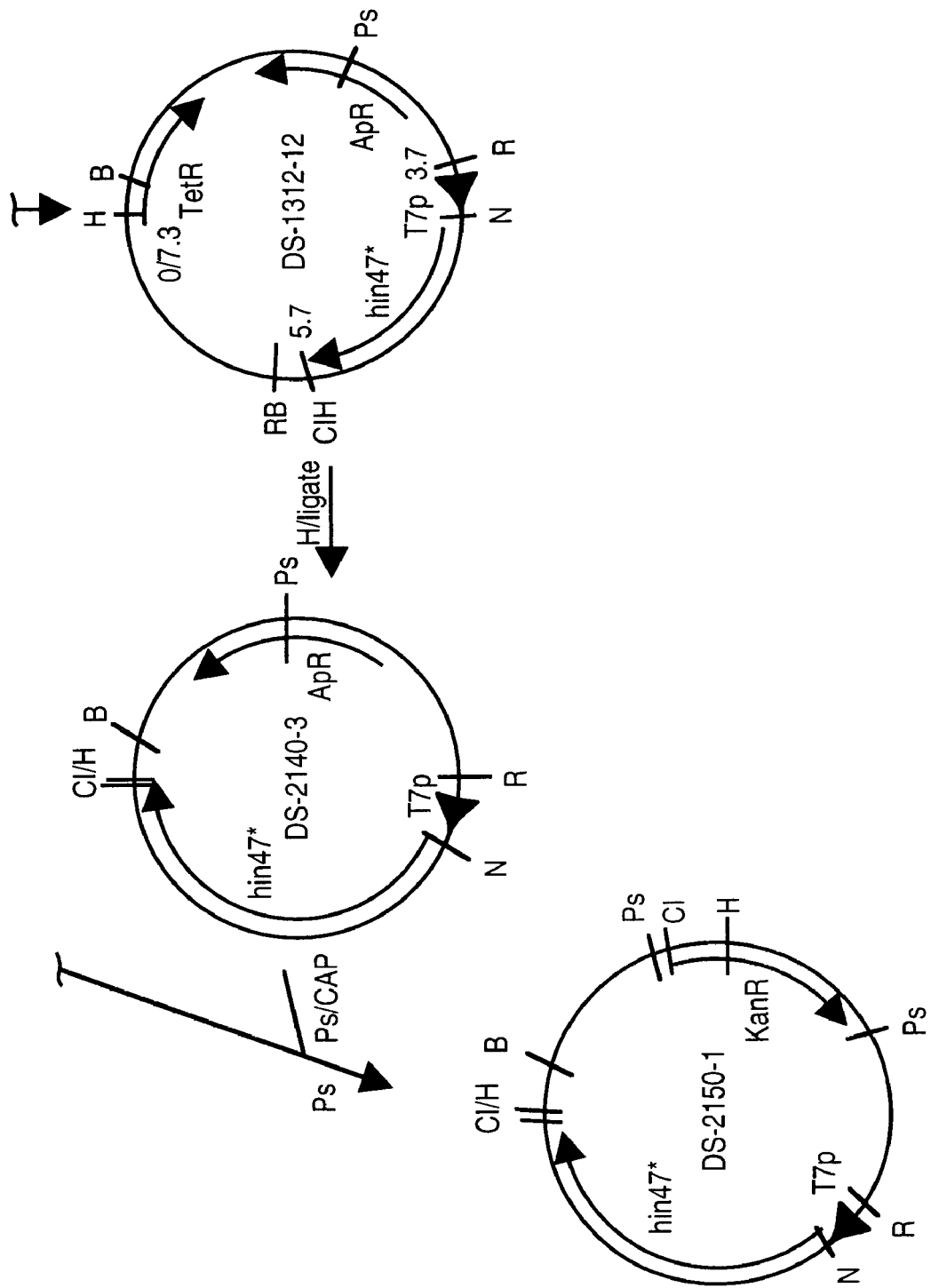

Referring to FIG. 1, there is illustrated the immune response in mice, to the H91A Hin47 antigen of a two component H91A Hin47+rHMW vaccine. High antibody titers are achieved with all vaccine combinations at the final bleed, but for the primary response at a low dose of H91A Hin47, there appears to be a difference between samples with or without rHMW. Referring to FIG. 2, there is illustrated the statistical analysis of the synergistic effect observed on the primary immune response to H91A Hin47, when increasing amounts of rHMW are added to a 0.3 $\mu$g dose of H91A Hin47.

Referring to FIG. 3, there is illustrated the immune response in mice, to the rHMW antigen of the two component H91A Hin47+rHMW vaccine. High antibody titers are achieved at final bleed with all vaccine combinations except those containing the lowest dose of rHMW. There is a dramatic decrease in anti-HMW antibody response when the 0.3 $\mu$g dose of rHMW is combined with increasing amounts of H91A Hin47. There appears to be a difference in the primary antibody response when the highest dose of rHMW is combined with increasing amounts of H91A Hin47. Referring to FIG. 4, there is illustrated the statistical analysis of the synergistic effect on the primary immune response to a 10 $\mu$g dose of rHMW combined with increasing amounts of H91A Hin47.

Referring to FIG. 5, there is illustrated the immune response in guinea pigs to the H91A Hin47 component of H91A Hin47+rHMW combination vaccines. There is no statistical difference in the anti-H91A Hin47 response to any of the vaccines. Referring to FIG. 6, there is illustrated the immune response in guinea pigs to the rHMW component of H91A Hin47+rHMW combination vaccines. There is no statistical difference in the anti-HMW response to any of the vaccines.

Referring to FIG. 7, there is illustrated the protection afforded by a H91A Hin47+rHMW combination vaccine in the intrabulla challenge model of otitis media, compared to the protection afforded by the H91A Hin47 component alone. Both vaccines are partially protective. Referring to FIG. 8, there is illustrated the protection afforded by a H91A Hin47+rHMW combination vaccine in the nasopharyngeal colonization model, compared to protection by the rHMW component alone. Both vaccines are highly protective.

Referring to FIG. 9, there is illustrated the stability profile of a H91A Hin47+rHMW vaccine at days 0 and 14. The two antigens remain adsorbed on the alum at the later time point and are not degraded.

Referring to FIGS. 10A and 10B, there is illustrated the immune response in guinea pigs, to the H91A Hin47 and rHMW antigens of the two component *H. influenzae* vaccine given alone or co-administered with Pentacel (diphtheria toxoid+tetanus toxoid+polio type 1+polio type 2+polio type 3+PRP-T+acellular pertussis vaccine comprised of pertussis toxoid+filamentous hemagglutinin+69 kDa/pertactin+fimbrial agglutinogens). There is also illustrated the immune response to the Pentacel antigens given alone or co-administered with the two component *H. influenzae* vaccine. There is no significant synergistic or suppressive effect of the co-administered multi-component vaccines.

Biological Deposits

Certain vectors that contain nucleic acid coding for a high molecular weight protein of a non-typeable strain of *Haemophilus* that are described and referred to herein have been deposited with the America Type Culture Collection (ATCC) located at 10801 University Boulevard, Manassas, Va. 20110-2209, USA, pursuant the Budapest Treaty and prior to the filing of this application. Samples of the deposited vectors will become available to the public and all restrictions imposed or access to the deposits will be received upon grant of a patent based on this United States patent application. In addition, the deposit will be replaced if viable samples cannot be dispensed by the Depository. The invention described and claimed herein is not limited in scope by the biological materials deposited, since the deposited embodiment is intended only as an illustration of the invention. Any equivalent or similar vectors that contain nucleic acid which encodes equivalent or similar antigens as described in this application are within the scope of the invention.

| Deposit Summary | | |
| --- | --- | --- |
| Plasmid | ATCC | Deposited Date |
| BK-76-1-1 | 203261 | Sep. 25, 1998 |

EXAMPLES

The above disclosure generally describes the present invention. A more complete understanding can be obtained by reference to the following specific Examples. These Examples are described solely for purposes of illustration and are not intended to limit the scope of the invention. Changes in form and substitution of equivalents are contemplated as circumstances may suggest or render expedient. Although specific terms have been employed herein, such terms are intended in a descriptive sense and not for purposes of limitations.

Methods of molecular genetics, protein biochemistry, immunology and fermentation technology used, but not explicitly described in this disclosure and these Examples, are amply reported in the scientific literature and are well within the ability of those skilled in the art.

Example 1

This Example describes the preparation of the H91A Hin47 vaccine component.

The H91A Hin47 mutant was prepared as described in U.S. Pat. No. 5,506,139. Briefly, an oligonucleotide 5' ATCAATAACAGCATTATTGGT 3' (SEQ ID NO: 1) was synthesized which would change the Histidine residue at 91 to an Alanine (ref. 17).

Plasmid JB-1276-1-2 is a pUC-based plasmid containing the T7/hin47 gene on an EcoR I fragment and was used to clone the hin47 gene into M13 mp18 for site-directed mutagenesis with the In Vitro Site-Directed Mutagenesis kit from Amersham. The preparation of plasmid JB-1276-1-2 is described in U.S. Pat. No. 5,506,139. The mutation of the His91 codon to Ala91 was confirmed by local sequencing. The H91A mutant hin47 gene was subcloned into pT7-7 to generate plasmid DS-1277-19 (FIG. 11).

The H91A Hin47 expression plasmid (DS-1277-19) utilizes ampicillin selection. The T7/H91A hin47 gene was cloned into pBR328 so that tetracycline selection could be used. Vector DS-1312-12 was thus a pBR328-based plasmid which contained the T7/H91A hin47 gene sequences between EcoR I and Cla I sites, having functional ampicillin and tetracycline resistance genes and containing a repeat of the Hind III-BamH I sequences which are found in both pBR328 and pEVvrfl.

A new plasmid based upon DS-1312-12 was constructed which utilizes kanamycin selection. The construction scheme is shown in FIG. 11. Plasmid DNA from DS-1312-12 was digested with Hind III generating two fragments. The larger 5.9 kb fragment contained a promoterless tetR gene, the ampR gene and the T7/H91A hin47 gene and was re-ligated on itself creating vector DS-2140-3. Plasmid DS-2140-3 was digested with Pst I and the kanR gene from plasmid pUC-4K (P-L Biochemicals) was inserted into the Pst I site, generating plasmid DS-2150-1 which is kanR and sensitive to both ampicillin and tetracycline.

Plasmid DNA from DS-2150-1 was prepared from a 50 mL culture using a protocol based upon the Holmes and Quigley procedure (ref. 18) and including extractions with phenol and chloroform. $E.$ $coli$ BL21(DE3) cells were made electrocompetent as follows. Briefly, 10 mL of overnight culture were inoculated into 500 mL of YT medium and the cells were grown at 37° C. with shaking until they reached an $A_{620}$=0.540. The culture was chilled on ice for 30 min., spun at 5K rpm for 15 min., and the cell pellet resuspended in 500 mL ice cold sterile water. The cell suspension was centrifuged as before and the cell pellet resuspended in 250 mL ice cold sterile water. The cell suspension was spun again, and the cells were resuspended in 10 mL of 10% glycerol. The glycerol suspension was spun, and the cells were resuspended in 1.5 mL of 10% glycerol, aliquotted as 40 µl samples, and stored at −70° C.

One aliquot of electrocompetent BL21(DE3) cells was thawed on ice and approximately 9 ng of DS-2150-1 DNA was added. Samples were incubated on ice for 3 min. then transferred to a −20° C. BioRad Gene Pulser electrode cuvette and subjected to an electric pulse. 900 µl of SOC medium were added and the mixture transferred to a culture tube where it was incubated at 37° C. for 1 hour before being plated onto YT agar containing 25 µg/mL kanamycin. The plate was incubated overnight at 37° C. and single colonies were used for expression studies.

Individual clones were grown in NZCYM medium to an $A_{600}$ nm of approximately 0.3 and lactose was added to 1% to induce expression. Cells were grown for 4 hours, then harvested and analysed by SDS PAGE. Clone DS-2171-1-1 was chosen as a representative clone which expressed high levels of H91A Hin47.

The $E.$ $coli$ containing DS-2171-1-1 was grown in 2×2 L flasks containing 250 mL of ECGM (containing 8 g/L glucose, pH 6.5) and incubated by shaking at 37° C. for approximately 9 hours in the dark at 250 rpm. The culture fluid (2×250 mL) was inoculated into a 10 L fermentor and the culture grown at 37° C. After approximately 10 hours of incubation, 1% lactose (final concentration) is added for induction, followed by an additional 4 hours incubation.

The culture fluid was harvested into sterile transfer bottles and concentrated and diafiltered by cross-flow filtration against 50 mM Tris/HCl buffer, pH 8.0. The cells in the concentrate are lysed using a high-pressure homogenizer (2 passes at 15,000 psi) to release the H91A Hin47 protein. The cell debris was removed by centrifugation at 15,000 rpm for 1.5 hours. The supernatant was further clarified by centrifugation and filtered through a 0.22 µm dead-end filter. Products may be stored frozen at −70° C. until further processing.

Sodium chloride (NaCl) was added to the clarified sample to a final concentration of 100 mM. The sample was then purified on an anion exchange chromatography column (TMAE-Fractogel) equilibrated with 50 mM Tris pH 8.0 containing 100 mM NaCl. The H91A Hin47 protein was obtained in the run-through.

The aqueous layer was loaded onto a ceramic hydroxyapatite type 1 (CHTP-1) column equilibrated with 10 mM sodium phosphate buffer pH 8.0. The column was then washed with 150 mM sodium phosphate buffer pH 8.0 and H91A Hin47 was eluted with 175 mM sodium phosphate buffer, pH 8.0 containing 1 M NaCl.

The H91A Hin47 purified protein was concentrated using a 10 kDa molecular weight cut-off membrane followed by diafiltration with approximately 10 volumes of phosphate buffered saline (PBS), pH 7.5.

The H91A Hin47 purified protein in PBS was passed through a Q600 sartobind membrane adsorber. After passing the solution, the membrane was regenerated using 1.0 M KCl/1.0 M NaOH followed by washing with 1 M KCl then equilibrating with PBS. The process was repeated twice. The concentrated diafiltered H91A Hin47 protein was sterile filtered through a 0.22 µm membrane filter. Sterile H91A Hin47 protein was adjuvanted with aluminum phosphate. The adosrbed purified concentrate was diluted to produce the adsorbed bulk at 100 µg/mL.

Example 2

This Example describes the preparation of the rHMW vaccine component.

The production and purification of the HMW protein has been described in copending U.S. patent application Ser. No. 09/167,568 filed Oct. 7, 1998.

Briefly, plasmid pHMW1-15 (ref. 10) contains a Xba I-site within the T7 promoter sequence and a unique BamH I site within the coding sequence of the mature HMW1A protein of non-typeable $Haemophilus$ strain 12. The 1.8 kb Xba I-BamH I fragment of pHMW1-15 was deleted and replaced by an approximately 114 bp Xba I-BamH I fragment generated from oligonucleotides. The resultant 11.3 kb plasmid, DS-1046-1-1, thus contains the T7 promoter joined in frame with the hmw1ABC operon that encodes the mature 125 kDa HMW1A protein (FIG. 11).

Plasmid DS-1046-1-1 contains the T7 hmw1ABC gene cassette and has a unique Bgl II site outside the coding region of the mature HMW1A gene. Plasmid DS-2224-1-4 contains the $E.$ $coli$ cer gene located on a BamH I fragment. This fragment was isolated and ligated into the Bgl II site of plasmid DS-1046-1-1 to produce plasmid BK-35-4 (FIG. 11). The kanamycin resistance cassette was excised from pUC 4K by Sal I restriction and ligated into the Sal I restricted BK-35-4 plasmid to produce plasmid BK-76-1-1.

Plasmids were introduced into $E.$ $coli$ BL21(DE3) cells by electroporation using a BioRad apparatus. Strains were grown at 37° C. in NZCYM medium to an optical density of $A_{578}$=0.3, then induced by the addition of lactose to 1.0% for 4 hours. Samples were adjusted to 0.2 OD/µl with SDS- PAGE lysis+loading buffer and the same amount of protein sample was loaded onto SDS-PAGE gels.

Figure 12:
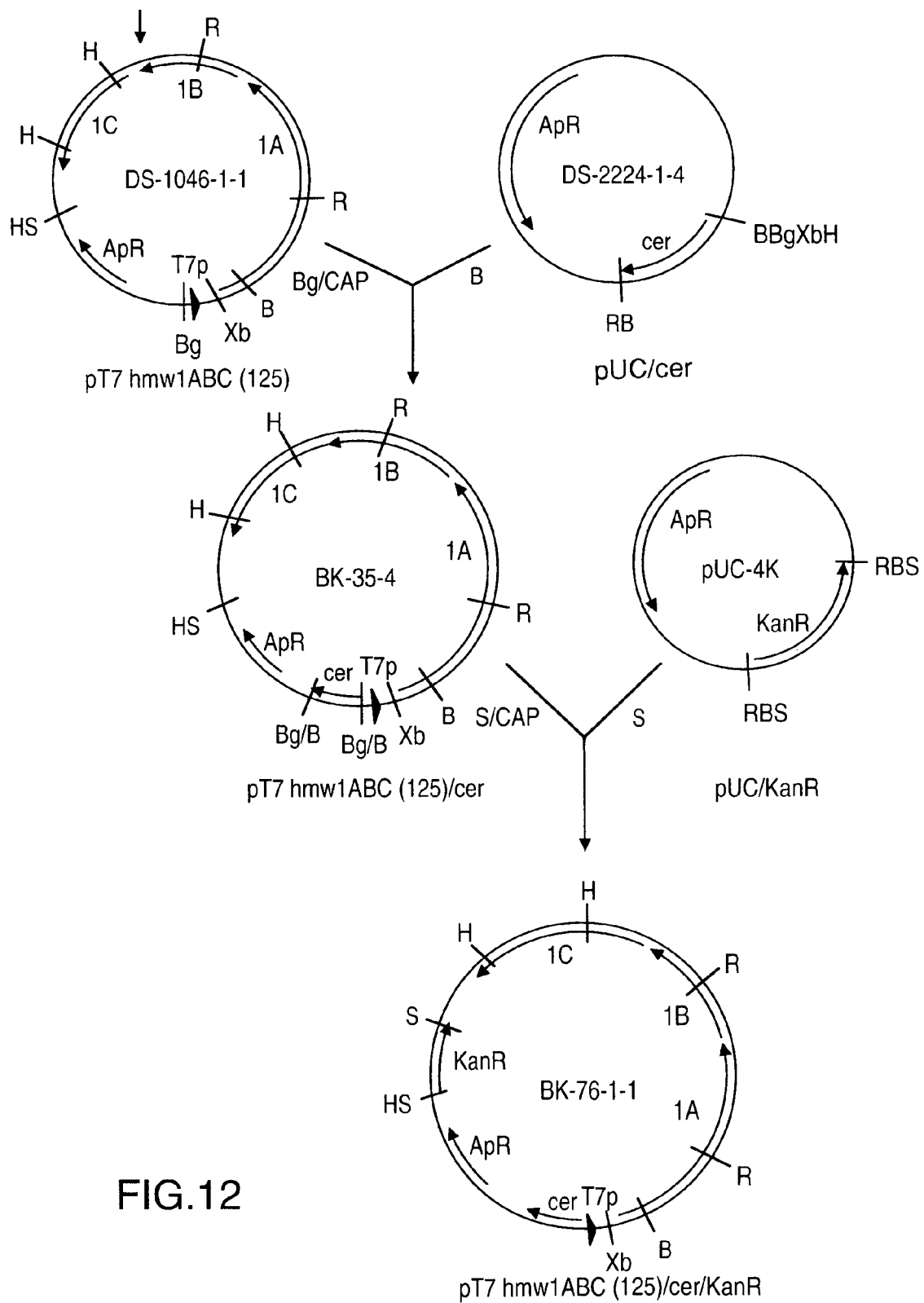
FIG. 12 shows a construction scheme for the preparation of plasmid BK-76-1-1 containing the hmw1ABC gene under control of the T7 promoter.

Recombinant HMW protein was expressed as inclusion bodies in *E. coli*, and were purified by the same procedure (FIG. 12) *E. coli* cell pellets from 500 ml culture were resuspended in 50 ml of 50 mM Tris-HCl, pH 8.0, containing 0.1 M NaCl, and disrupted by sonication. The extract was centrifuged at 20,000 g for 30 min and the resultant supernatant was discarded. The pellet was further extracted, in 50 ml of 50 mM Tris-HCl, pH 8.0 containing 0.5% Triton X-100 and 10 mM EDTA, then centrifuged at 20,000 g for 30 min, and the supernatant was discarded. The pellet was further extracted in 50 ml of 50 mM Tris-HCl, pH 8.0, containing 1% octylglucoside, then centrifuged at 20,000 g for 30 min, and the supernatant was discarded.

The resultant pellet, obtained after the above extractions, contains the inclusion bodies. The pellet was solubilized in 6 ml of 50 mM Tris-HCl, pH 8.0, containing 6 M guanidine and 5 mM DTT. Twelve ml of 50 mM Tris-HCl, pH 8.0 was added to this solution and the mixture was centrifuged at 20,000 g for 30 min. The supernatant was precipitated with polyethylene glycol (PEG) 4000 at a final concentration of 7%. The resultant pellet was removed by centrifugation at 20,000 g for 30 min and the supernatant was precipitated by $(NH_4)_2SO_4$ at 50% saturation. After the addition of $(NH_4)_2SO_4$, the solution underwent phase separation with protein going to the upper phase, which was then subjected to centrifugation at 20,000 g for 30 min. The resultant pellet was dissolved in 2 ml of 50 mM Tris-HCl, pH 8.0, containing 6 M guanidine HCl and 5 mM DTT and the clear solution was purified on a Superdex 200 gel filtration column equilibrated in 50 mM Tris-HCl, pH 8.0, containing 2 M guanidine HCl. The fractions were analysed by SDS-PAGE and those containing the purified rHMW1 were pooled and dialysed overnight at 4° C. against PBS, then centrifuged at 20,000 g for 30 min. The protein remained soluble under these conditions and glycerol was added to the rHMW1 preparation at a final concentration of 20% for storage at −20° C.

The concentration of the rHMW vaccine component was adjusted to 400 $\mu$g ml$^{-1}$ in PBS (pH 7.3) and was adjuvanted with aluminum phosphate to a final concentration of 3 mg ml$^{-1}$. Different doses were prepared by diluting the stock with 3 mg ml$^{-1}$ of aluminum phosphate in PBS.

Example 3

This Example describes the combination of H91A Hin47 and rHMW as a two component vaccine.

Vaccines were prepared that comprised combinations of H91A Hin47 and rHMW as set forth in the following Table II:

TABLE II

| | $\mu$g rHMW | | | | | | | |
|---|---|---|---|---|---|---|---|---|
| $\mu$g H91A↓ | 0 | 0.3 | 1.0 | 3.0 | 10 | 25 | 50 | 100 |
| 0 | | m | m | m | m | gp | gp | gp |
| 0.3 | m | m | m | m | m | | | |
| 1.0 | m | m | m | m | m | | | |
| 3.0 | m | m | m | m | m | | | |
| 25 | gp | | | | | gp | gp | qp |
| 50 | gp | | | | | gp | gp | gp |
| 100 | gp | | | | | gp | gp | gp |

Notes:
m indicates the vaccine was used to immunize mice.
gp indicates that the vaccine was used to immunize guinea pigs.

Vaccine components were combined on day 0, mixed overnight at 4° C. and aliquotted on day 1. The combined vaccines were stored at 4° C. throughout the immunization period.

Example 4

This Example describes the analysis of the immunogenicity of the multi-component vaccines in animals.

Groups of five BALB/c mice (Charles River, Quebec) were immunized subcutaneously (s.c.) on days 1, 29 and 43 with one of the mouse vaccines described in Example 3. Blood samples were taken on days 0, 14, 28, 42, and 56.

Groups of 5 Hartley outbred guinea pigs (Charles River, Quebec) were immunized intramuscularly (i.m.) on days 1, 29 and 43 with one of the guinea pig vaccines described in Example 3. Blood samples were taken on days 0, 14, 28, 42, and 56.

Anti-H91A Hin47 and anti-rHMW IgG antibody titers were determined by antigen specific enzyme linked immunosorbent assays (ELISAs). Microtiter wells (Nunc-MAXISORB, Nunc, Denmark) were coated with 50 $\mu$l of protein solution (0.4 $\mu$g ml$^{-1}$ for H91A Hin47 or 0.4 $\mu$g ml$^{-1}$ for rHMW). The secondary antibodies used were affinity-purified F(ab')$_2$ fragments of goat anti-mouse IgG (Fc-specific) or anti-guinea pig IgG (Fc-specific) antibodies conjugated to horseradish peroxidase (Jackson ImmunoResearch Labs, Mississauga, Ontario). The reactions were developed using tetramethylbenzidine (TMB/H2O2, ADI, Mississauga, Ontario) and absorbancies were measured at 450 nm (using 540 nm as a reference wavelength) in a Flow Multiskan MCC microplate reader (ICN Biomedicals, Mississauga, Ontario). The reactive titer of an antiserum was defined as the reciprocal of the dilution consistently showing a two-fold increase in absorbance over that obtained with the pre-bleed serum sample.

Figure 2:
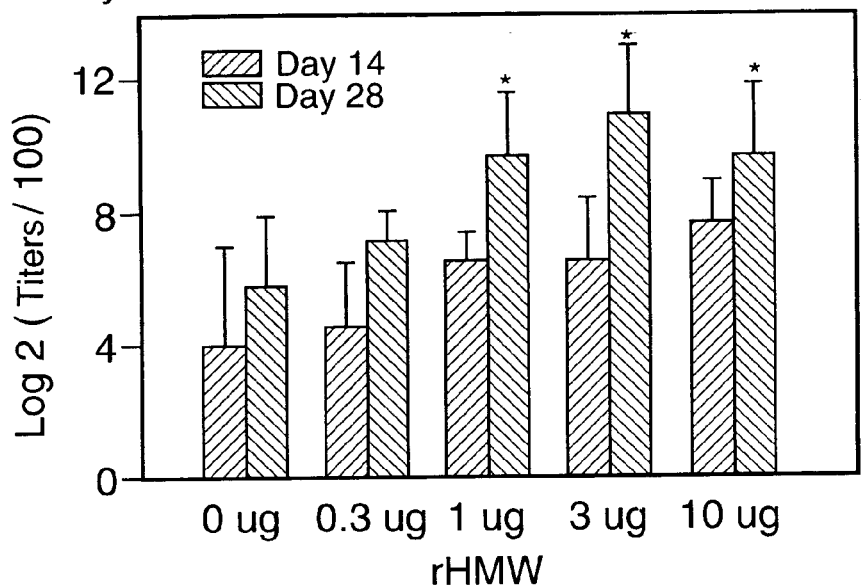
FIG. 2 is a bar graph which shows the synergistic effect on the primary immune response to a low dose (0.3 μg) of H91A Hin47 by the addition of rHMW.

The results of the immunogenicity studies are illustrated in FIGS. 1 to 6. As shown in FIG. 1, the final bleed sera obtained from mice immunized with 0.3, 1.0 or 3.0 $\mu$g of H91A Hin47 all had high antibody titers to H91A Hin47, irrespective of the amount of rHMW present (0 to 10 $\mu$g). However, there is a statistically significant difference in the primary anti-H91A Hin47 responses. As shown in FIG. 2, there is an enhanced primary response to H91A Hin47 in the presence of increasing amounts of rHMW. These findings are surprising and indicate that rHMW is exhibiting a synergistic effect on the primary immune response to H91A Hin47.

Figure 3:
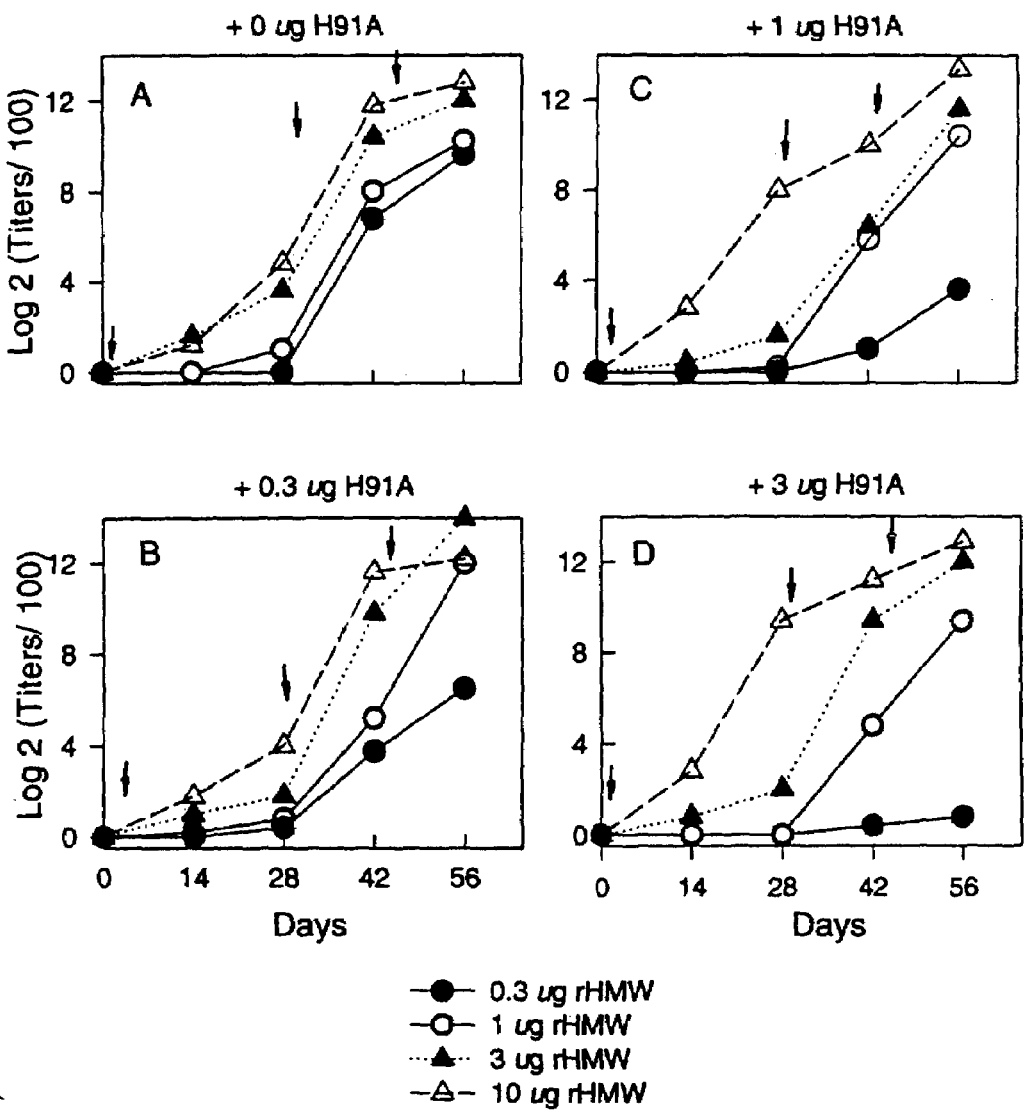
FIG. 3, having Panels A to D, shows the anti-rHMW immune responses for H91A Hin47+rHMW combination vaccines in mice. Panel A, no added H91A Hin47; panel B, 0.3 μg of H91A Hin47 added; panel C, 1.0 μg of H91A Hin47 added; panel D, 3.0 μg of H91A Hin47 added. The arrows indicate the timing of the immunizations.
Figure 4:
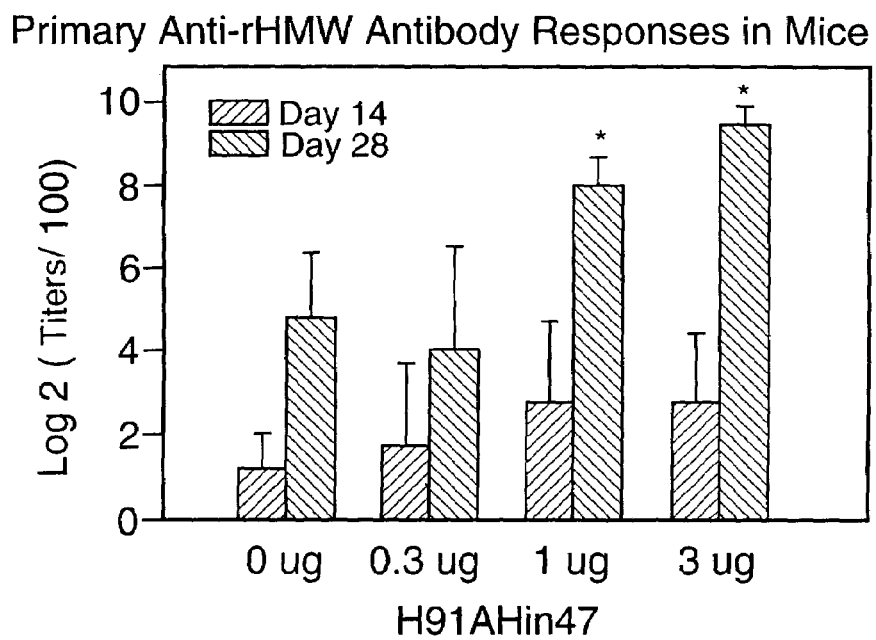
FIG. 4 is a bar graph which shows the synergistic effect on the primary immune response in mice to a high dose (10 μg) of rHMW by the addition of H91A Hin47.

As shown in FIG. 3, the final bleed sera obtained from mice immunized with 1, 3 or 10 $\mu$g of rHMW all had high antibody titer to rHMW, irrespective of the amount of H91A Hin47present (0 to 3 $\mu$g). However, at the lowest dose of rHMW (0.3 $\mu$g), there is a statistically significant inhibition of the immune response to rHMW with increasing amounts of H91A Hin47 added. This finding is surprising and suggests that H91A Hin47 acts as an immune suppressor for low doses of rHMW. On the contrary, at the highest dose of rHMW (10 μg), the addition of H91A Hin47 significantly enhances the immune response to rHMW (FIG. 4). These findings in mice, indicate that the relative amounts of the two components, H91A Hin47 and rHMW, are critical to obtain a good immune response to both antigens.

From the data presented herein, it would appear that about 3 to about 10 μg of rHMW, most preferably about 10 μg, shows the enhanced effect with about 1 to about 3 μg of H91A Hin47.

Figure 5:
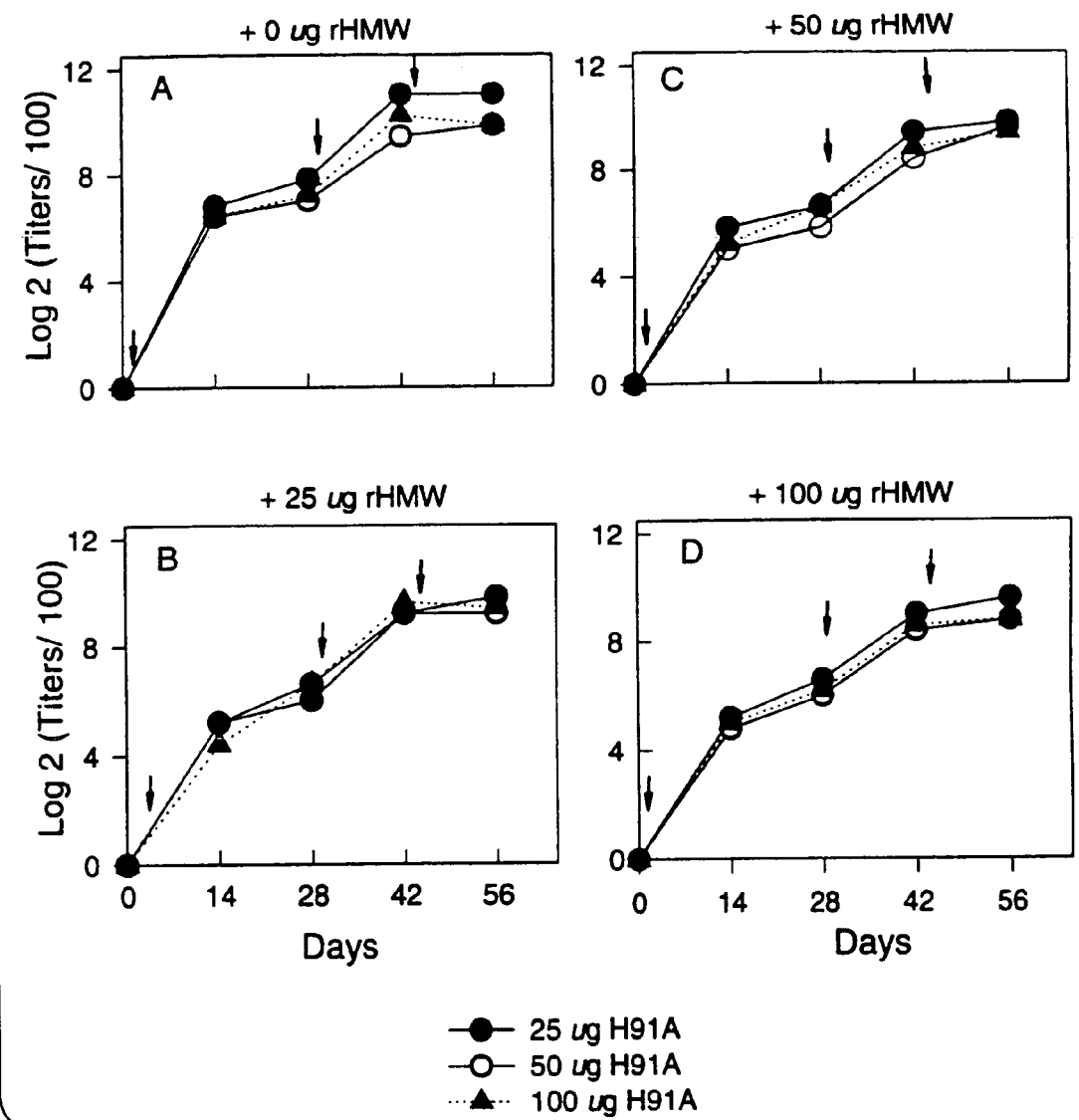
FIG. 5, having Panels A to D, shows the anti-H 91A Hin47 immune responses for H91A Hin47+rHMW combination vaccines in guinea pigs. Panel A, no added rHMW; panel B, 25 μg of rHMW added; panel C, 50 μg of rHMW added; panel D, 100 μg of rHMW added. The arrows indicate the timing of the immunizations.
Figure 6:
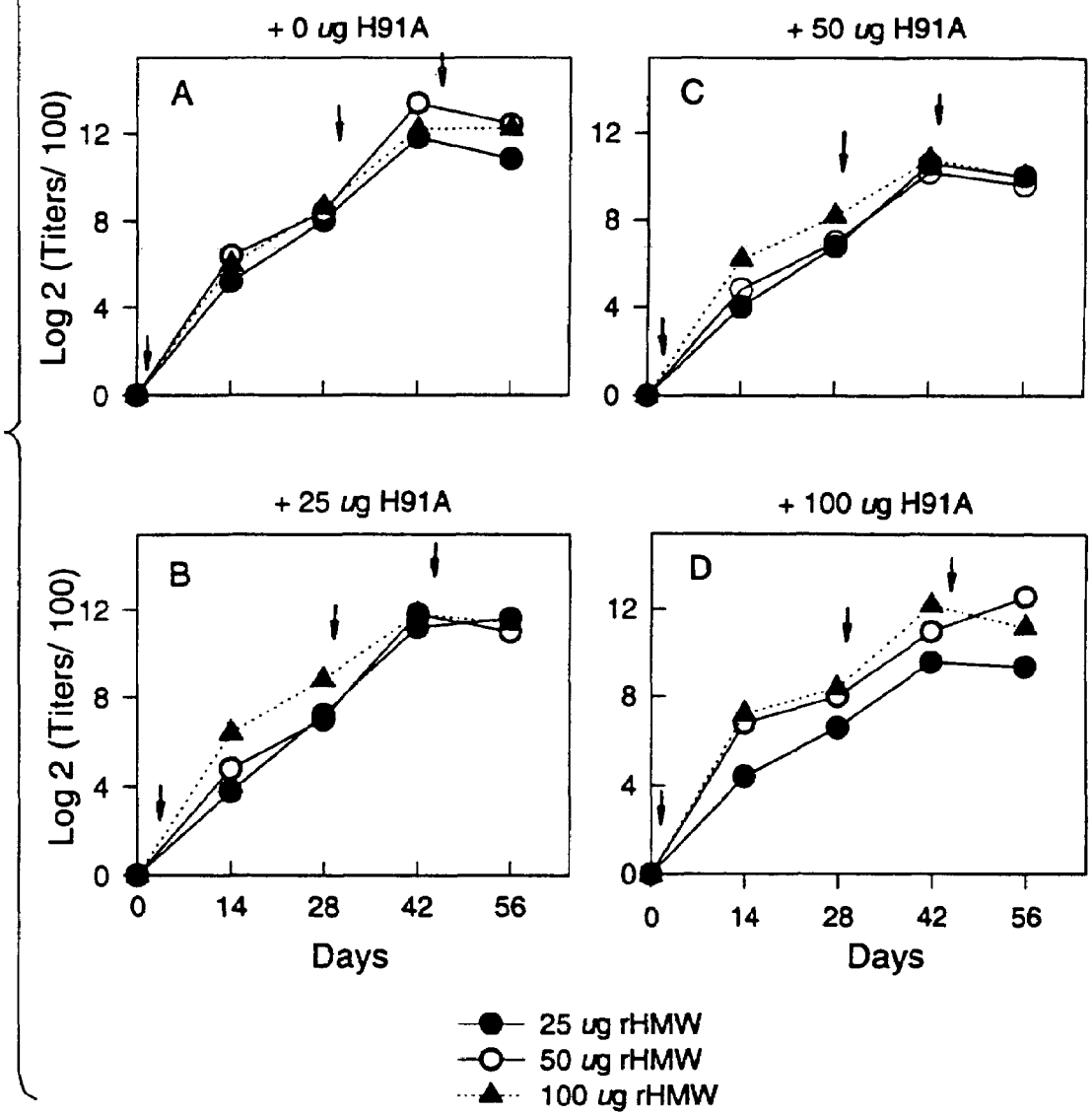
FIG. 6, having Panels A to D, shows the anti-rHMW immune responses for H91A Hin47+rHMW combination vaccines in guinea pigs. Panel A, no added H91A Hin47; panel B, 25 μg of H91A Hin47 added; panel C, 50 μg of H91A Hin47 added; panel D, 100 μg of H91A Hin47 added. The arrows indicate the timing of the immunizations.

FIG. 5 shows the anti-H91A Hin47 antibody titers obtained in guinea pigs. The addition of rHMW had no effect on the anti-H91A Hin47 antibody titers. Similarly, the addition of H91A Hin47 had no effect on the anti-rHMW antibody titers in guinea pigs (FIG. 6).

Example 5

This Example describes the protective ability of a multi-component vaccine in animal models of disease.

Figure 7:
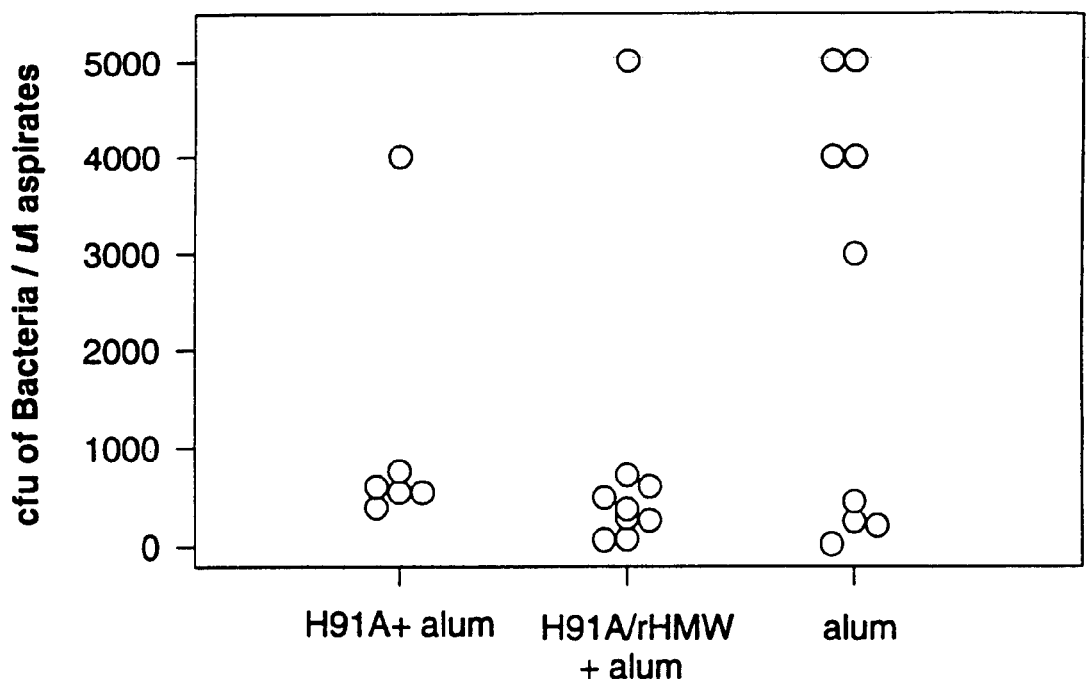
FIG. 7 shows the protection of the H91A Hin47+rHMW combination vaccine in the chinchilla model of otitis media.

H91A Hin47 is partially protective in the chinchilla model of otitis media, as described in the aforementioned U.S. Pat. No. 5,506,139. In this model, 1 to 2 year old chinchillas (Moulton Chinchilla Ranch, Rochester, Minn.) are immunized i.m. on days 0, 14 and 28 with 30 μg of H91A Hin47 adsorbed to alum, and challenged on day 44 with 50 to 350 cfu of live organisms delivered into the middle ear space via the epitympanic bulla (ref. 11). Animals are monitored by tympanometry and middle ear fluid is collected 4 days post challenge, mixed with 200 μl of BHI medium and dilutions plated onto chocolate agar plates that are incubated for 24 h at 37° C. Convalescent animals or those mock-immunized with alum alone, are used as controls. For the multi-component vaccine study, 50 μg of H91A Hin47 was mixed with 50 μg of rHMW as described in Example 3 and chinchillas were immunized as described. The results of the protection study are shown in FIG. 7 which indicates that there is still partial protection afforded in the intrabulla challenge model by the combination of H91A Hin47+rHMW.

In young chinchillas, it has been demonstrated that nasopharyngeal colonization with non-typeable *H. influenzae* leads to otitis media (ref. 14). rHMW is partially protective in a chinchilla nasopharyngeal colonization challenge model, as described in the aforementioned U.S. patent application Ser. No. 09/167,568. In this model, animals are immunized i.m. on days 0, 14 and 28 with 25, 50 or 100 μg of rHMW adsorbed to alum, and challenged on day 44 with $10^8$ cfu of live bacteria delivered intranasally (50 μl per nares).

Figure 8:
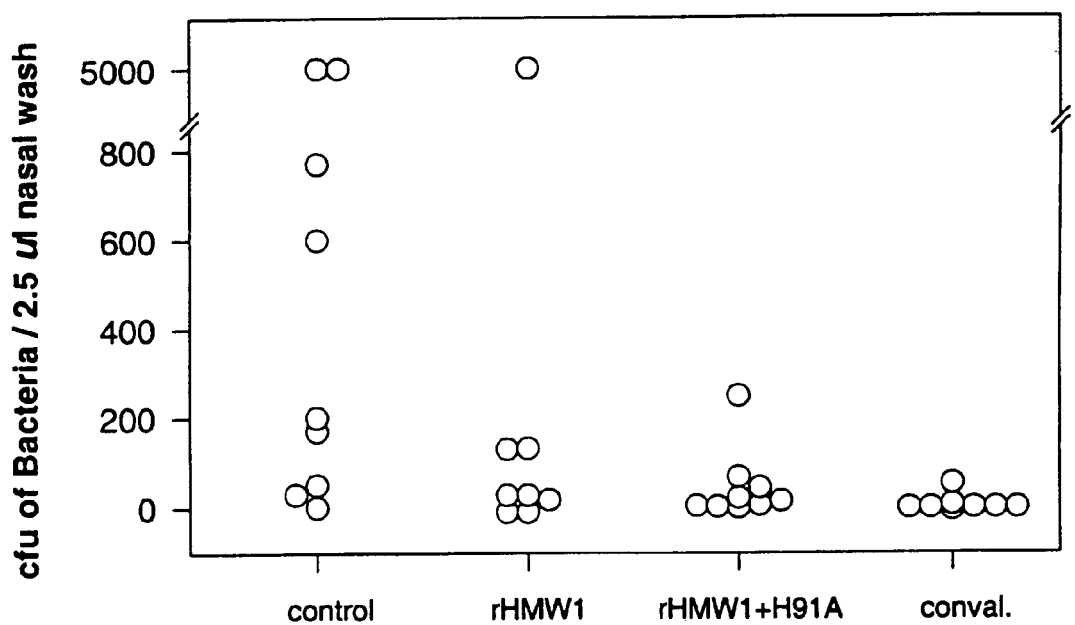
FIG. 8 shows the protection of the H91A Hin47+rHMW combination vaccine in the chinchilla model of nasopharyngeal colonization.

Nasopharyngeal lavage is performed 4 days post challenge using 1 ml of sterile saline as wash. 25 μl of wash is plated onto chocolate agar in the presence of streptomycin and the plates incubated at 37° C. for 24 h. (The challenge strain was made streptomycin resistant by serial passaging, in order to facilitate the quantitation of recovered bacteria in the presence of natural flora that are killed by the streptomycin.) Convalescent animals or those mock-immunized with alum alone, are used as controls. For the multi-component vaccine study, 50 μg of rHMW was mixed with 50 μg of H91A Hin47 as described in Example 3 and chinchillas were immunized as described. The results of the protection study are shown in FIG. 8 which indicates that there is still excellent protection afforded in the nasopharyngeal colonization challenge model by the combination of H91A Hin47+rHMW.

Example 6

This Example describes the analysis of the stability of the two component vaccine.

Figure 9:
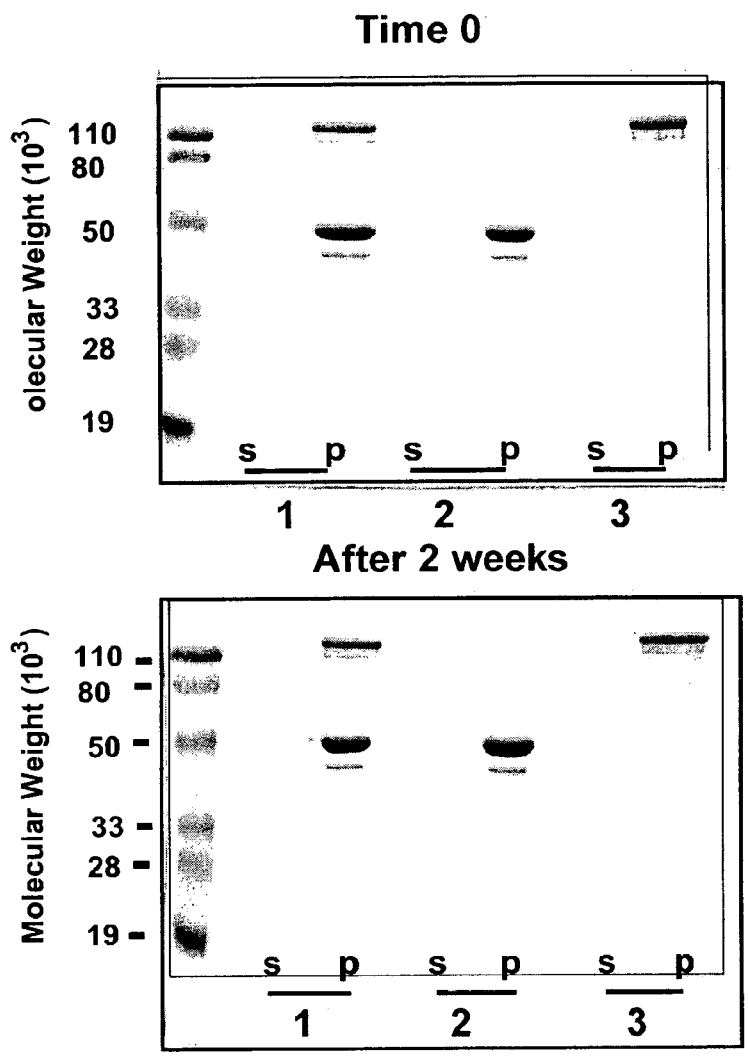
FIG. 9 having Panels A and B, are SDS-PAGE analyses showing the stability profile of the H91A Hin47+rHMW combination vaccine on day 0 (Panel A) and 14 (Panel B), compared to the individual components.

The adsorbed H91A Hin47 (400 μg protein+3 mg aluminum phosphate per ml) and rHMW (400 μg protein+3 mg aluminum phosphate per ml) were mixed 1:1 to a final concentration of 100 μg of each protein+3 mg aluminum phosphate per ml as described in Example 3. The individually adsorbed H91A Hin47 and rHMW proteins were also adjusted to a final concentration of 100 μg of protein+3 mg aluminum phosphate/ml. Samples were stored at 4° C. and 0.5 ml aliquots were taken on day 0 and every two weeks for analysis by SDS-PAGE. Aliquots were microfuged at 10,000 rpm for 10 min to separate the supernatant from the alum pellet. The pellet was dissolved in SDS-PAGE sample buffer and the supernatant was first precipitated with acetone, then dissolved in SDS-PAGE sample buffer. Equivalent amounts of supernatant and pellet were analyzed assuming that the protein was either 100% adsorbed or unadsorbed. The results of the stability study are shown in FIG. 9 which indicates that after two weeks, there is no degradation of the proteins and both are still fully adsorbed to the alum.

Example 7

This Example illustrates the immune response to co-administration of the two component *H. influenzae* vaccine with Pentacel®.

Groups of 5 Hartley guinea pigs (Charles River, Quebec) were immunized i.m. on days 1 and 21 with one of H91A Hin47+rHMW two-component vaccine, Pentacel vaccine (a commercial vaccine of Connaught Laboratories Limited containing PT+FHA+69 kDa+Aggs at weights of 20:20:5:3 μg; diphtheria toxoid at 15 Lf; tetanus toxoid at 5 Lf; IPV containing types 1, 2 and 3 inactivated poliovirus at 40, 8 and 32 D-antigen units respectively; 10 μg of PRP-T conjugate of *H. influenzae* type B polysaccharide conjugated to tetanus toxoid at 20 μg), or H91A Hin47+rHMW two-component vaccine+Pentacel. The two-component vaccine contained 50 μg each of H91A Hin47 and rHMW. The animals receiving the two component+Pentacel vaccines had injection on both flanks. Blood samples were taken on day 1, prior to injection and then on day 28.

Figure 10A:
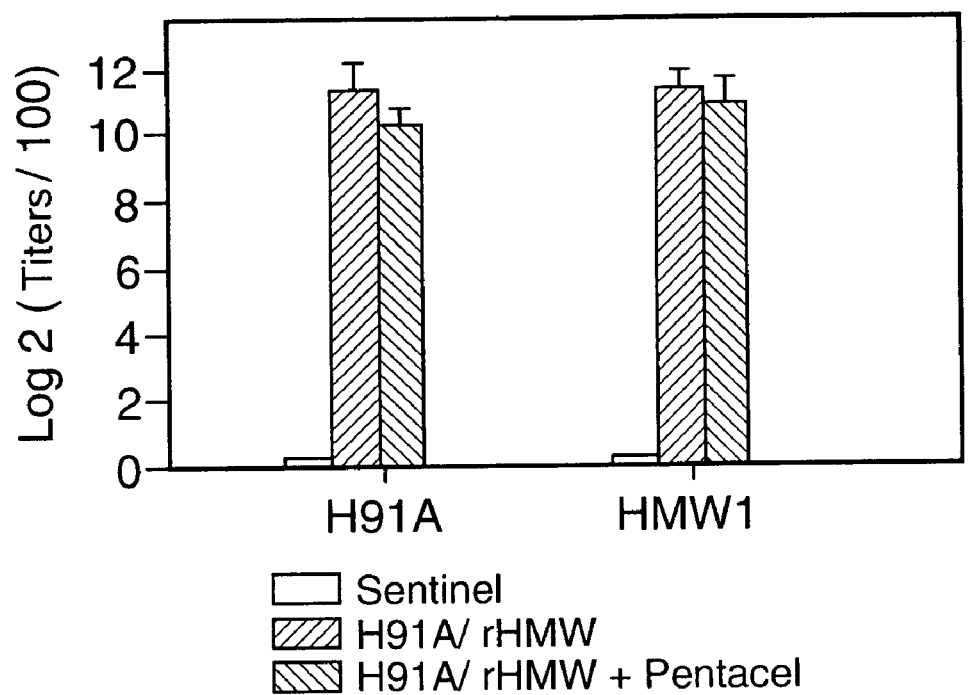
FIG. 10A is a bar graph of the immune response to H91A and rHMW in the presence and absence of Pentacel.
Figure 10B:
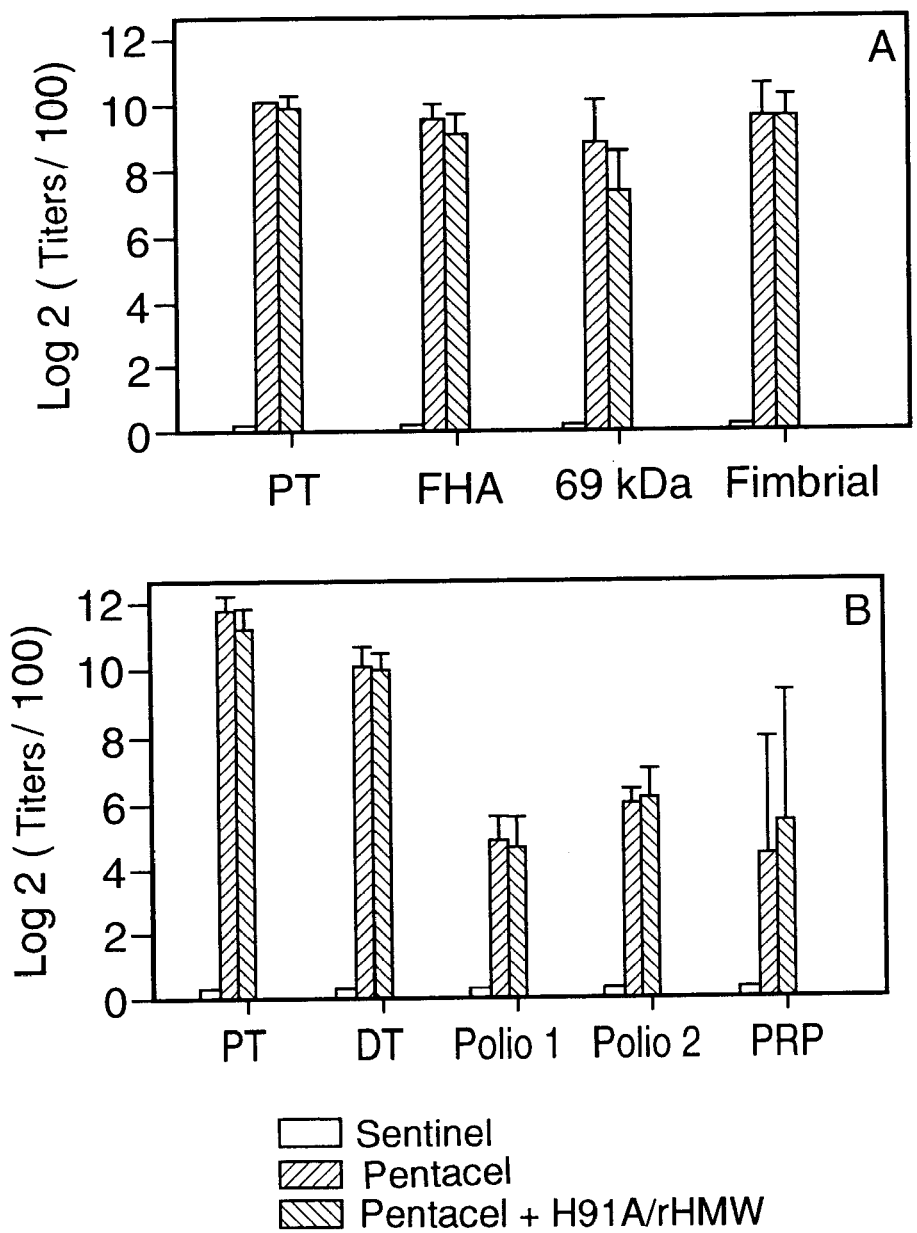
FIG. 10B, having Panels A and B, contains a bar graphs of the immune response to pertussis toxoid (PT), filamentous haemagglutinin (FHA), pertactin (69 kDa), fimbrial agglutinogens (Panel A), tetanus toxoid (TT), diphtheria toxoid (DT), polio type 1, polio type 2 and PRP-T (Panel B) in Pentacel® when the Pentacel® is administered alone or with the two component H91A+rHMW *H. influenzae* vaccine.

Anti-H91A Hin47 and anti-rHMW IgG antibody titers were determined by ELISA as described in Example 4. Anti-Pentacel component IgG antibody titers were determined by ELISA, essentially as described in Example 4. Microtiter plates were coated with 5 μg ml$^{-1}$ of antigen for PT, FHA 69 kDa, Aggs, and PRP; 1/20 dilution of 2.5 Lf ml$^{-1}$ for diphtheria toxoid; 1.3 Lf ml$^{-1}$ for tetanus toxoid; 1/50 dilution of 25.6 EU ml$^{-1}$ for polio type 1; or 1/50 dilution of 15.1 EU ml$^{-1}$ for polio type 2. A signal to noise ratio for polio type 3 could not be established. The secondary antibody used was F(ab)'$_2$ fragments of donkey anti-guinea pig IgG (H+L) conjugated to horseradish peroxidase (Jackson ImmunoResearch Labs). Negative controls were pre-bleed sera or antiserum to an irrelevant antigen from RSV. The results are seen in FIGS. 10A and 10B.

SUMMARY OF THE DISCLOSURE

In summary of this disclosure, the present invention provides a multi-component vaccine against *Haemophilus influenzae* having a wide spectrum of efficacy and comprising two different antigens of *Haemophilus influenzae*, one of which antigens is an adhesin Modifications are possible within the scope of the invention.

REFERENCES

1. Barbour, M. L., R. T. Mayon-White, C. Cole, D. W. M. Crook, and E. R. Moxon. 1995. The impact of conjugate vaccine on carriage of *Haemophilus influenzae* type b. J. Infect. Dis. 171:93–98.
2. Berkowitz et al. 1987. J. Pediatr. 110:509.
3. Claesson et al. 1989. J. Pediatr. 114:97.
4. Black, S. B., H. R. Shinefield, B. Fireman, R. Iliatt, M. Polen, E. Vittinghoff, The Northern California Kaiser Permanent Vaccine Study Center Pediatrics Group. Efficacy in infancy of oligosaccharide conjugal,) *Haemophilus influenzae* type b (HBOC) vaccine in a United States population of 61,080 children. 1991. Pediatr. Infect. Dis. J. 10:97–104.
5. Nitta, D. M., M. A. Jackson, V. F. Burry, and L. C. Olson. 1995. Invasive *Haemophilus influenzae* type f disease. Pediatr. Infect. Dis J. 14:157–160.
6. Waggoner-Fountain, L. A., J. O. Hendley, E. J. Cody, V. A. Perriello, and L. G. Donowitz. 1995. The emergence of *Haemophilus influenzae* types e and t as significant pathogens. Clin. Infect. Dis. 21:1 122–1324.
7. Madore, D. V. 1996. Impact of immunization on *Haemophilus influenzae* type b disease. Infectious Agents and Disease 5:8–20.
8. Bluestone, C. D. 1982. Current concepts in otolaryngology. Otitis media in children: to treat or not to treat? N. Engi. J. Med. 306:1399–1404.
9. Barenkamp, S. J., and F. F. Bodor. 1990. Development of serum bactericida activity following non-typable *Haemophilus influenzae* acute otitis media. Pediatr. Infect. Dis. 9:333–339.
10. Barenkamp, S. J., and J. W. St. Geme III. 1994. Genes encoding high-molecular weight adhesion proteins of non-typeable *Haemophilus influenzae* are part of gene clusters. Infect. Immun. 62:3320–3328.
11. St. Geme III J. W., V. V. Kumar, D. Cutter, and S. J. Barenkamp. 1998. Prevalence and distribution of the hmw and hia genes and the HMW and Hia adhesins among genetically diverse strains of non-typeable *Haemophilus influenzae*. Infect. Immun. 66:364–368
12. St. Geme III, J. W., S. Falkow, and S. J. Barenkamp. 1993. High-molecular-weight proteins of non-typeable *Haemophilus influenzae* mediate attachment to human epithelial cells. Proc. Natl. Acad. Sci. USA 90:2875–2879.
13. Barenkamp, S. J. 1996. Immunization with high-molecular-weight adhesion proteins of non-typeable *Haemophilus influenzae* modifies experimental otitis media in chinchillas. Infect. Immun. 64:1246–1251.
14. Yang, Y. P., S. M. Loosmore, B. Underdown, and M. H. Klein. 1998. Nasopharyngeal colonization with non-typeable *H. influenzae*, in chinchillas. Infect. Immun. 66:1973–1980.
15. Young and Davis, 1985, Gene 38: 31 to 38.
16. Retzlaff, C., Y. Yamamoto, P. S. Hoffman, H Friedman, and T. W. Klein. 1994. Bacterial heat shock proteins directly induce cytokine mRNA and interleukin-1 secretion in macrophage cultures. Infect. Immun. 62:5689–5693.
17. Loosmore, S. M., Y-P. Yang, R. Oomen, J. M. Shortreed, D. C. Coleman, and M. H. Klein. 1998. The *Haemophilus influenzae* HtrA protein is a protective antigen. Infect. Immun. 66:899–906.
18. Holmes, D. S. and Quigley, M. 1981. A rapid boiling method for the preparation of bacterial plasmids. Anal. Biochem. 114:193–197.

What we claim is:

1. An immunogenic composition for conferring protection in a host against disease caused by *Haemophilus influenzae*, which comprises:

an analog of *Haemophilus influenzae* Hin47 protein having a decreased protease activity which is less than about 10% of that of natural Hin47 protein, and a high molecular weight (HMW) protein of a strain of non-typeable *Haemophilus influenzae*.

2. The composition of claim 1 wherein said HMW protein is present in said composition in an amount which enhances the immune response in the host to the Hin47 protein.

3. The composition of claim 2 wherein said HMW protein is present in the said amount while the individual immunogenicities of the proteins in the composition is not impaired.

4. The composition of claim 1 wherein said analog of Hin47 protein is one in which at least one amino acid of the natural Hin47 protein contributing to protease activity has been deleted or replaced by a different amino acid and which has substantially the same immunogenic properties as natural Hin47 protein.

5. The composition of claim 4 wherein said at least one amino acid is selected from the group consisting of amino acids 91, 121 and 195 to 201 of natural Hin47 protein.

6. The composition of claim 5 wherein Serine-197 is replaced by alanine.

7. The composition of claim 5 wherein Histidine-91 is replaced by alanine, lysine or arginine.

8. The composition of claim 7 wherein Histidine-91 is replaced alanine.

9. The composition of claim 5 wherein Asp-121 is replaced by alanine.

10. The composition of claim 3 wherein said HMW protein is an HMW1 or HMW2 protein of a non-typeable strain of *Haemophilus influenzae*.

11. The composition of claim 10 wherein the HMW1 and HMW2 proteins are produced recombinantly.

12. The composition of claim 10 wherein said HMW1 and HMW2 proteins are derived from the respective strain of non-typeable *Haemophilus influenzae* and possess respective molecular weights as set forth in the following Table:

| Molecular | Non-typeable *H. influenzae* Strain | | | | | |
|---|---|---|---|---|---|---|
| Weight (kDa) | 12 | JoyC | K21 | LCDC2 | PMH1 | 15 |
| Mature Protein: | | | | | | |
| HMW1 | 125 | 125.9 | 104.4 | 114.0 | 102.4 | 103.5 |
| HMW2 | 120 | 100.9 | | 111.7 | 103.9 | 121.9 |

13. The composition of claim 1 further comprising an adjuvant.

14. The composition of claim 13 wherein said adjuvant is aluminum hydroxide or aluminum phosphate.

15. The composition of claim 1 comprising about 25 to about 100 μg of the Hin47 protein analog, and about 25 to about 100 μg of the HMW protein.

16. The composition of claim 1 further comprising at least one additional antigenic component for conferring protection against infection caused by another pathogen.

17. The composition of claim 16 wherein said at least one additional antigenic component is selected from the group consisting of diphtheria toxoid, tetanus toxoid, pertussis antigens, non-virulent poliovirus and a conjugate of a tetanus or diphtheria toxoid and a capsular polysaccharide of *Haemophilus influenzae*.

18. The composition of claim 17 wherein said pertussis antigens are selected from the group consisting of pertussis toxoid, filamentous hemagglutinin, pertactin and agglutinogens.

19. A method of immunizing a host against disease caused by infection with *Haemophilus influenzae*, including otitis media, which comprises administering to the host an immunoeffective amount of the composition as claimed in claim 1.

* * * * *